(12) United States Patent
D'Hondt

(10) Patent No.: US 6,991,929 B1
(45) Date of Patent: Jan. 31, 2006

(54) HEPATITIS A VACCINES

(75) Inventor: Erik D'Hondt, Ottenburg (BE)

(73) Assignee: SmithKline Beecham Biologicals S.A., Rixensart (BE)

( * ) Notice: Subject to any disclaimer, the term of this patent is extended or adjusted under 35 U.S.C. 154(b) by 0 days.

(21) Appl. No.: 09/807,659

(22) PCT Filed: Oct. 8, 1999

(86) PCT No.: PCT/EP99/07765

§ 371 (c)(1),
(2), (4) Date: May 17, 2001

(87) PCT Pub. No.: WO00/23574

PCT Pub. Date: Apr. 27, 2000

(30) Foreign Application Priority Data

Oct. 16, 1998 (GB) .............................. 9822714

(51) Int. Cl.
*C12N 7/02* (2006.01)

(52) U.S. Cl. ..................... 435/235.1; 435/41; 435/239
(58) Field of Classification Search .............. 435/235.1, 435/239, 41, 325
See application file for complete search history.

(56) References Cited

U.S. PATENT DOCUMENTS

| 4,702,909 A | 10/1987 | Villarejos et al. |
| 5,268,292 A | 12/1993 | Robertson et al. |
| 5,776,468 A | 7/1998 | Hauser et al. |

FOREIGN PATENT DOCUMENTS

| GB | 2 099 700 | 12/1982 |
| WO | WO 95/17209 | 6/1995 |

OTHER PUBLICATIONS

Millman, et al., "Australia Antigen (A Hepatitis–Associated Antigen). Purification and Physical Properties", *Journal of Experimental Medicine*, 131(6): 1190–1199, (1970).

André, et al., "Inactivated Candidate Vaccines for Hepatitis A", *Progress in Medical Virology*, 37: 72–95, (1990).

Bishop, et al., "Rapid and Efficient Purification of Hepatitis A Virus from Cell Culture", *Journal of Virological Methods*, 47(1–2): 203–216, (1994).

*Primary Examiner*—Laurie Scheiner
(74) *Attorney, Agent, or Firm*—William R. Majarian; Stephen Venetianer; Charles M. Kinzig

(57) ABSTRACT

A process for the production of inactivated Hepatitis A virus substantially free of host cell contamination is described, the process comprising: a) culturing Hepatitis A virus and harvesting a Hepatitis A preparation; b) treating said Hepatitis A preparation with a protease; and thereafter c) separating intact virus from protease digested material; d) inactivating said virus. Also described are vaccines comprising the inactivated Hepatitis A virus, preferably in combination with strong adjuvants.

5 Claims, 4 Drawing Sheets

Figure 1A:
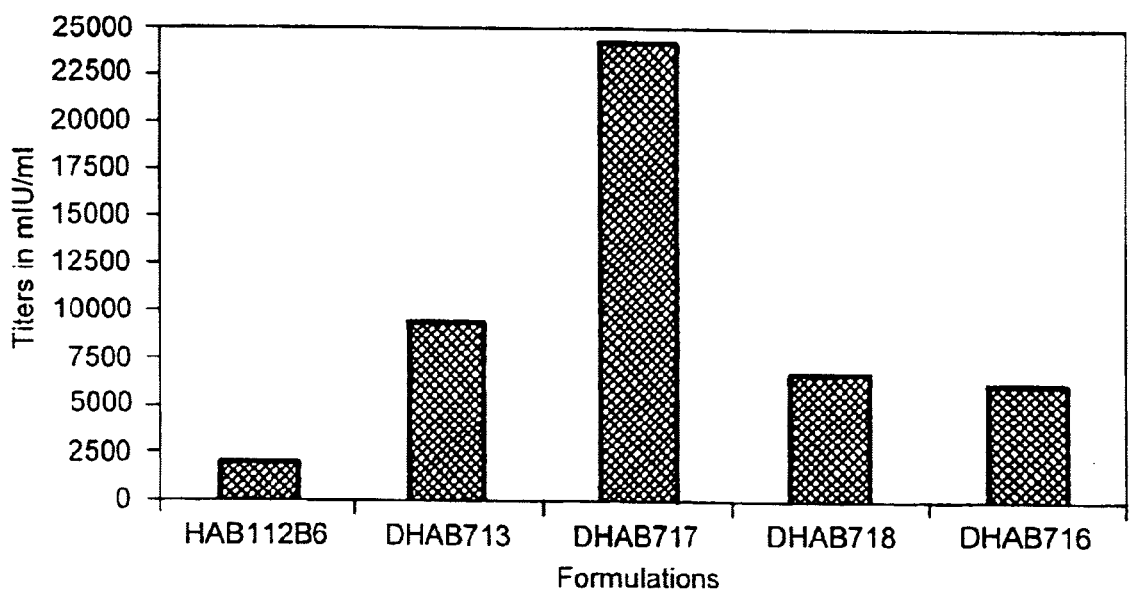

| 1 | HAB112B6 | HB20/AlPO4 + HA720/Al(OH)3 |
| 2 | DHAB713 | HB20/AlPO4 / MPL50 + HA1440/Al(OH)3 |
| 3 | DHAB717 | HB20/AlPO4 + MPL50/Al(OH)3 + HA720/Al(OH)3 |
| 4 | DHAB718 | HB20/AlPO4 + MPL50/AlPO4 + HA720/Al(OH)3 |
| 5 | DHAB716 | HB20/AlPO4 / MPL50 + HA720/Al(OH)3 |

1) Response on pool on 28 days post I

SDS PAGE of HAV pool before (utilising Andre et al PROCESS) & after the MMP process of example 1b (HAV-MMP)

SDS PAGE of HAV pool before (andre et al) & after the process of example 1a
with twostep permetion chromatography (HAV-MMP)
Proteins are fractionated on 12.5% SDS-PAGE. They are visualized by silver staining Lane 1: Low MW standards (14.4, 21.5, 31.0, 45.0, 66.2, 97.4kDa)
   Lane 2 to 8: HAV-MMP (lots 6029 to 6032 and 6034 to 6036)
   Lane 9: Andre et al (lot 5010)

Note:-lot numbers refer to distinct virus pools
   -Scan of a gel photograph

HEPATITIS A VACCINES

The present invention relates to new vaccine compositions, processes for their manufacture and their use in medicine. In particular, the present invention relates to improved Hepatitis A vaccines adjuvanted with a potent immunostimulator, preferably such as monophosphoryl lipid A or a derivative thereof. The invention also relates to combination vaccines in which the Hepatitis A vaccine is a component.

Hepatitis A vaccines are known. For example the vaccine Havrix (Trade Mark), from SmithKline Beecham Biologicals can be used to prevent hepatitis A infections and is also formulated with aluminium hydroxide as adjuvant. This vaccine is produced according to the procedure of Andre et al. It comprises an attenuated strain of the HM-175 Hepatitis A virus inactivated with formol (formaldehyde); see Andre et al [Prog Med. Virol. 1990, vol 37; -p72–95].

The vaccine Twinrix (Trade Mark) which is a combination of the above hepatitis A and hepatitis B antigens may be used to protect against Hepatitis A and Hepatitis B simultaneously. The vaccine Hepatyrix (Trade Mark) which is a combination of the above hepatitis A antigen and a *Salmonella typhimurium* purified Vi polysaccharide may be used to protect against Hepatitis and typhoid simultaneously.

International patent application WO93/19780 (SmithKline Beecham Biologicals s.a.) discloses, inter alia, a Hepatitis A vaccine adjuvanted with 3D-MPL.

European patent 0 339 667 (Chemo Sero) describes the general concept of combining a hepatitis A antigen and a hepatitis B antigen to make a combination vaccine. In that specification it is stated that the adjuvant which is used is not critical: it must only be capable of enhancing the immune activity to a desired extent and not cause any side effects. It is stated that aluminium gel may be used, in particular aluminium hydroxide gel and aluminium phosphate gel.

It has now been found that traditional processes for producing and purifying inactivated virus for hepatitis A vaccines can leave a small residue of contaminants from the host cells in which the hepatitis A virus was grown. Such host cell contaminants, especially when they are from human origin, diploid in nature and at a low level, provide no concern when the vaccine is adjuvanted with aluminium salts. But when the vaccine is adjuvanted with strong immunostimulants there is a theoretical possibility that a vaccinee may raise an adverse immune response to the host contaminants.

Accordingly there is a need for a method of manufacture which removes substantially all traces of such host cell proteins.

Accordingly in one aspect of the invention there is provided a process for the production of inactivated Hepatitis A virus substantially free of host cell contamination, the process comprising:

a) culturing Hepatitis A virus and harvesting a hepatitis A preparation;

b) treating said hepatitis A preparation with a protease; and thereafter c) separating intact virus from protease-digested material;

d) inactivating said virus.

Surprisingly, the protease digestion treatment does not adversely affect the Hepatitis A virus, but facilitates the breakdown and separation of host cell contaminants from the Hepatits A preparation.

Preferably the Hepatitis A virus is derived from HM-175 strain.

By substantially free of host cell contamination is meant that less than 10%, preferably less than 8%, more preferably less than 5% host cell protein can be detected by scanning of silver-stained SDS PAGE. More importantly and as determined by slot blot hybridisation one dose of HAV in the vaccine preferably contains less than 10 ng of host cell proteins.

Preferably the protease used is trypsin. Other proteases that may be utilised include pronase, papain, and pepsin.

The protease treatment is preferably carried out at above room temperature, e.g. at about 37° C for about 2 hrs.

The separation of the intact virus from the protease and the digested components can be achieved by a variety of suitable methods, for example by permeation chromatography.

Alternatively the protease and digested components may be separated by any separation method that separates on the basis of size, for example ultra filtration.

The product can then be further purified by other steps to remove other contaminants. For example, the product can be further purified by subjecting the product to ion-exchange chromatography to remove any nucleic acid residue.

It is believed that the protease digestion step of the method according to the invention can improve purification of the hepatitis A preparation due to two effects. First, the protease digests any contaminating host proteins such that they are easier to separate in the chromatographic separation step that follows the protease treatment. Second, the digestion of contaminating host proteins allows better separation of other contaminating materials which would otherwise be associated with undigested host proteins, in particular nucleic acid, in the ion exchange step. It will be appreciated that these observed effects do not necessarily limit the invention in any way.

In another aspect of the present invention there is provided an inactivated Hepatitis A virus substantially free of contaminating host proteins, as defined above.

The inactivated hepatitis A virus may then be formulated into a vaccine.

Thus the invention provides in a further aspect a Hepatitis A vaccine comprising an inactivated hepatitis A virus substantially free of host cell contaminants.

Such a vaccine may advantageously include a suitable adjuvant. Suitable adjuvants include an aluminium salt such as aluminium hydroxide gel or aluminium phosphate, but may also be a salt of calcium, iron or zinc, or may be an insoluble suspension of acylated tyrosine, or acylated sugars, cationically or anionically derivatised polysaccharides, or polyphosphazenes.

Advantageously, the highly purified hepatitis A virus may be formulated with strong adjuvant systems. Thus in the formulation of the invention, it is preferred that the adjuvant composition induces an immune response comprising Th1 aspects.

In general terms, a Th1-type response is characterised by the production of IFN-y as 10 opposed to a Th2-type response which is characterised by the production of cytokines such as IL-4, IL-5 and IL-10. The isotypic profile of the humoral response can also be used as a marker for Th1 or Th2-type responses. In mice Th1-type responses are often associated with the generation of antibodies of the IgG2*a* subtype while IgG1 are markers of a Th2-type response. The situation is not as clear in humans but data suggest that IgG1 and IgG4 could respectively be markers of Th1- and Th2-type responses.

Suitable adjuvant systems include for example a combination of monophosphoryl lipid A, preferably 3-O-deacylated monophosphoryl lipid A (3D-MPL), and preferably formulated together with an aluminium salt.

An enhanced system involves the combination of monophosphoryl lipid A and a saponin derivative particularly the combination of QS21 and 3D-MPL as disclosed in WO 94/00153, or a less reactogenic composition where the QS21 is quenched with cholesterol as disclosed in WO 96/33739.

A particularly potent adjuvant formulation involving QS21, 3D-MPL and d,1-alpha-tocopherol in an oil in water emulsion is described in WO 95/17210.

Other known adjuvants which may be included are CpG containing oligonucleotides for example as disclosed in WO 96/02555.

Accordingly in a preferred embodiment of the present invention there is provided a vaccine comprising a virus of the present invention, adjuvanted with monophosphoryl lipid A or a derivative thereof.

Preferably the vaccine additionally comprises a saponin, more preferably QS21.

Preferably the formulation additionally comprises an oil in water emulsion and d, 1-alpha-tocopherol.

Figure 1B:
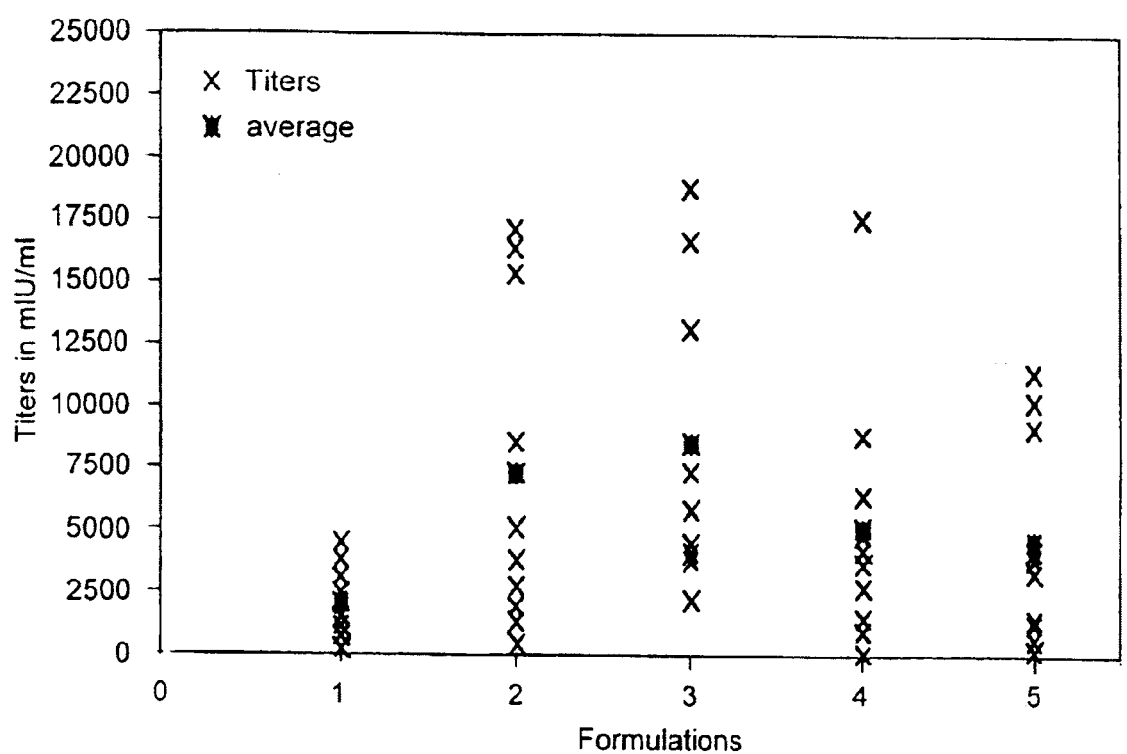

The present invention also provides a method for producing a vaccine formulation comprising mixing a purified virus of the present invention together with a pharmaceutically acceptable excipient or carrier, such as 3D-MPL.

The purified virus of the invention may advantageously be combined with other antigens so that it is effective in the prophylaxis or treatment of other diseases in addition to hepatitis A infections. A preferred combination involves a combination containing a hepatitis B antigen.

The preparation of Hepatitis B surface antigen (HBsAg) is well documented. See, for example, Harford et al in *Develop. Biol. Standard* 54, page 125 (1983), Gregg et al in *Biotechnology,* 5, page 479 (1987), EP-A-0 226 846, EP-A-0 299 108 and references therein.

As used herein the expression 'Hepatitis B surface antigen' or 'HBsAg' includes any HBsAg antigen or fragment thereof displaying the antigenicity of HBV surface antigen. it will be understood that in addition to the 226 amino acid sequence of the HBsAg S antigen (see Tiollais et al, *Nature,* 317, 489 (1985) and references therein) HBsAg as herein described may, if desired, contain all or part of a pre-S sequence as described in the above references and in EP-A-0 278 940. In particular the HBsAg may comprise a polypeptide comprising an amino acid sequence comprising residues 12–52 followed by residues 133–145 followed by residues 175–400 of the L-protein of HBsAg relative to the open reading frame on a Hepatitis B virus of ad serotype (this polypeptide if referred to as L*; see EP 0 414 374). HBsAg within the scope of the invention may also include the preS1–preS2-S polypeptide described in EP 0 198 474 (Endotronics) or analogues thereof such as those described in EP 0 304 578 (McCormick and Jones). HBsAg as herein described can also refer to mutants, for example the 'escape mutant' described in WO 91/14703 or EP 0 511 855 A1, especially HBsAg wherein there is an amino acid substitution at position 145 to arginine from glycine.

Normally the HBsAg will be in particle form. The particles may comprise for example S protein alone or may be composite particles, for example (L*,S) where L* is as defined above and S denotes the S-protein of HBsAg. The said particle is advantageously in the form in which it is expressed in yeast.

The invention in a further aspect provides a vaccine formulation as described herein for use in medical therapy, particularly for use in the treatment or prophylaxis of hepatitis viral infections. In a preferred aspect the vaccine accordingly to the invention is a therapeutic vaccine useful for the treatment of ongoing hepatitis infections, more especially hepatitis A and/or hepatitis B infections in humans suffering therefrom.

In view of the surprisingly efficacious results obtained, in a further preferred aspect the invention provides a vaccine composition for the treatment or prophylaxis of Hepatitis A and/or Hepatitis B infections.

Advantageously the hepatitis vaccine composition of the invention contains other antigens so that it is effective in the treatment or prophylaxis of one or more other bacterial, viral or fungal infections.

Accordingly the hepatitis vaccine formulation according to the invention preferably contains at least one other component which may be selected from non-hepatitis antigens which are known in the art to afford protection against one or more of the following diseases:

diphtheria, tetanus, pertussis, Haemophilus influenzae b (Hib), and polio.

Preferably the vaccine according to the invention includes HBsAg as hereinabove defined.

Suitable components for use in such combination vaccines are already commercially available and details may be obtained from the World Health Organization. For example the polio component may be the Salk inactivated polio vaccine (IPV). The pertussis vaccine component may comprise a whole cell or acellular product.

Advantageously the hepatitis or combination vaccine according to the invention is a paediatric or an adolescent vaccine.

Preferred combination vaccines according to the invention for adolescent use include one or more components selected from antigens which are known in the art to provide protection against one or more of the following diseases:

human papillomavirus (HPV), herpes simplex virus (HSV), Epstein Barr virus (EBV), Varicella Zoster virus (VZV), human cytomegalovirus (HCMV), *Toxoplasma gondii.*

The amount of each antigen in the vaccine dose is selected as an amount that induces an immunoprotective response without significant adverse side effects in typical vaccinees. Such amount will vary depending on which specific immunogens are employed. Generally it is expected that each dose will comprise 0.01 to 1.0 $\mu$g protein/dose for Hepatitis A, most preferably from between 0.06 to 0.220 $\mu$g protein/dose. For antigens other than Hepatitis A, for example HBsAg, HSV etc, the amount of protein per dose may be higher, e.g. up to about 20 $\mu$g per dose. An optimal amount of each of one or more immunogens for a particular vaccine can be ascertained by standard studies involving observation of antibody titres and/or other responses in subjects. Following an initial vaccination, subjects may receive a boost within about 4 weeks.

In a further aspect of the present invention there is provided a method of manufacture of a vaccine effective in preventing or treating hepatitis infection, wherein the method comprises mixing the hepatitis antigen as defined herein with MPL or a derivative thereof.

Using this method one or more additional components are preferably admixed with the inactivated Hepatitis A vaccine to provide a combination vaccine.

The following examples illustrate the invention and its advantages.

BRIEF DESCRIPTION OF THE DRAWINGS

FIG. 1A presents anti-HAV antibody titers from mice receiving HAV/HBs vaccine formulations.

FIG. 1B presents anti-HbsAg antibody titers from mice receiving HAV/HBs vaccine formulations.

FIG. 2 is an SDS-PAGE of HAV pool before (utilizing Andre et al process and after the MMP process of Example 1b (HAV-MMP) Early trypsin single permeation step process. Proteins are fractionated on 12.5.% SDS-PAGE. They are visualized by silver staining. Lane 1: Low MW standards (14.4, 21.5, 31.0, 45.0, 66.2, 97.4 kDa). Lane 2: Andre et al (lot 5199). Lane 3: Andre et al (lot 5200). Lane 4: Andre et al (lot 5201). Lane 5: HAV-MMP (lot 7199). Lane 6: HAV-MMP (lot 7200). Lane 7: HAV-MMP (lot 7201).

Figure 3:
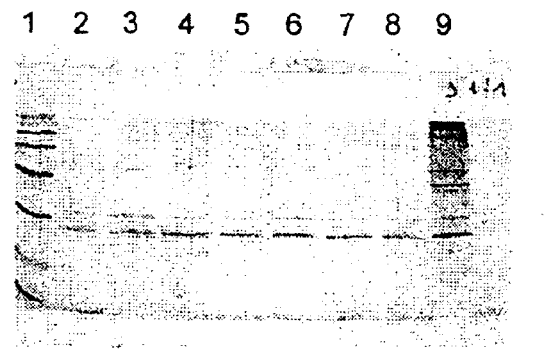

FIG. 3 is an SDS PAGE of HAV pool before (Andre et al) and after the process of example 1a with two step permeation chromatography (HAV-MMP). Proteins are fractionated on 12.5% SDS-PAGE. They are visualized by silver staining. Lane 1: Low MW standards (14.4, 21.5, 31.0, 45.0, 66.2, 97.4 kDa). Lane 2 to 8: HAV-MMP (lots 6029 to 6032 and 6034 to 6036). Lane 9: Andre et al (lot 5010).

EXAMPLES

Example 1 a) Purification Steps

The series of steps given in this Example may be performed in different combinations in accordance with the method according to the invention, but always involving a trypsin or other protease digestion step.

CULTURE AND HARVEST

Hepatitis A virus HM175 is cultured on MRC5 cells (Andre et al supra) and the virus is harvested after washing of the cell layer to remove serum used in growth media. After freeze/thaw a detergent (Tween 20) is added to extract the virus from the cell debris. Cell debris is removed by filtration through a 0.22 μm membrane. Filtrate is further subjected to ultra-filtration. The resulting concentrate can eventually be clarified by centrifugation at 5–10,000×g for 1–2 hours.

TRYPSINATION

The concentrate containing the HAV virus is treated with purified trypsin extracted from pig pancreas. The trypsin used is double crystallised and kept frozen before use. Before addition of trypsin the concentrate is prewarmed at 37° C. under constant agitation. Trypsin is then added at a ratio of 440 IU per ml of concentrate, and the mixture gently stirred for minimum 2 hrs at 37° C. (maximum 2.5hrs).

CONCENTRATION

After trypsin treatment the product can be processed without delay at ambient temperature on an ultrafiltration device in order to reduce the volume. The membrane used is regenerated cellulose with nominal cut-off of 30,000 Dalton, and up to a maximum of 8 ml of trypsinated product per cm$^2$ of membrane, is processed at a transmembrane pressure between 0.2 and 0.6 bar to achieve a concentration factor of between 8 and 12.

PERMEATION CHROMATOGRAPHY

The aim of this step is to separate proteins from the intact HAV virus. When a permeation chromatography step is conducted after trypsin treatment, conditions have to be adapted to eliminate residual trypsin as well. The separation gel used is Permeation Sepharose 4BFF.

The virus is eluted at a smaller retention volume than the smaller protein fragments which are eluted with larger retention volume (closer to the total volume of the column).

Chromatography parameters are as follows:

Chromatographic medium: Sepharose 4B FF (from Pharmacia)

Injected volume: 1 to 5% of gel volume

Elution rate: 5–10 cm/h

Temperature: 10 to 16° C.

Pool of fractions: target 100 ng prot/ 720 Elisa units (+/−10%)

ION EXCHANGE

The purpose of this purification step is to reduce the DNA content (originating from MRC5 cells). This step is run according to the batch principle.

The pool from the previous chromatographic step is adjusted to 0.3M NaCl and then mixed with the ion exchange resin under mild agitation for 1 hr (maximum 1.5 hr) at room temperature.

After DNA fixation the gel is eliminated by filtration. The unfixed HAV virus suspension is then diluted to adjust the NaCl concentration to 150 mM. Alternatively, the ion exchange purification step can also be conducted by column chromatography.

The final purified product is sterile filtered on 0.22 μm filter. Chromatographic parameters are as follows:

Load: 3% of gel compared to the volume of the pool (vol/vol).

Temperature: ambient

Inactivation is carried out as described in Andre et al, except that 0.22 μm of formol is used.

FORMALDEHYDE REDUCTION

Within 48 hr after the end of the inactivation the product is diafiltered and concentrated in order to reduce the formaldehyde content and to be preadsorbed on an aluminium salt (preferably aluminium hydroxide or aluminium phosphate).

Prior to use, the complete ultrafiltration device is sanitised with 0.1N NaOH for at least 30 minutes. The device is then thoroughly rinsed with diafiltration buffer and the membranes are then coated with a buffer containing amino acids (Travasol). Finally the device is rinsed with diafiltration buffer.

After diafiltration and concentration the final product is sterile filtered on a 0.22 μm filter.

b) Purification Schemes

The purification steps described above were combined in such a way that a pure product was obtained in an economical way. Two such purification schemes are presented in Scheme 1 both of which yield a similar product. In one configuration of the steps as shown in scheme 1 the steps were carried out in the order described in Example 1*a*, and in the other configuration the trypinisation step was carried out between the ultrafiltration and first permeation chromatography steps. This meant that the second permeation chromatography step could be eliminated.

Example 2

Characterisation

Samples of purified product were analysed by SDS PAGE 12.5 % acrylamide, 1% SDS in a stacking gel, migration for 15 h at 45–50 volts. The gel was stained with AgNO$_3$ and the colour was allowed to develop for 10 to 20 min and compared with traditional HAV processes (Andre et al).

As can be seen from FIGS. 2 and 3 by subjecting the product to protease treatment a majority of high molecular weight contaminants are removed.

Example 3

HAV Vaccine Formulations 3.1 HAV–alum 3D-MPL

The HAV particle of example 1 was first adsorbed on to aluminium hydroxide (superfos) followed by the addition of free 3D-MPL. A 0.5 ml dose 720 ELU of Hepatitis A virus particle 0,025 mg $Al^{3+}$ion and 50 μg of 3D-MPL.

3.2 HAV+Hbs Ag formulations

The following formulations were made:

1. Hep B S Ag 20 μg/AlPO$_4$+HA 720/Al(OH)$_3$
2. Hep B S Ag 20 μ/AlPO$_4$/3D-MPL 50 μg+HA 1440/Al(OH)$_3$
3. Hep B S Ag 20 μg/AlPO$_4$+3D-MPL 50 μg/Al(OH)$_3$+HA 720/Al(OH)$_3$
4. Hep B S Ag 20 μg/AlPO$_4$+3D-MPL 50 μg/AlPO$_4$+HA 720 Al(OH)$_3$
5. Hep B S Ag 20/AlPO$_4$/3D-MPL 50 μg+HA720/Al(OH)3

In group 1 the individual antigens were adsorbed on to the aluminium salt 0.025 mg $Al^{3+}$ ion (Al(OH)$_3$ Superfos) for HA, 0.475 mg Al13+ ion (AlP$_4$ Superfos type). In group 2 and 5, 50 μg/dose of free 3D-MPL was added to adsorbed Hepatitis S antigen to which the adsorbed hepatitis A component was added. In group 3 and 4, 3D-MPL was separately adsorbed on to the aluminium salt, and then the three adsorbed components were mixed together.

Example 4

Immunogenicity Experiments

Balb/c mice

Groups of 10 mice were immunised intramuscularly three times at 2 weeks interval with HAV/HBs formualtions (1/10 HD). Antibody response to Hbs were monitored by ELISA at 14 days post II and 14 days post III. The isotypic profile of the anti-HBs response was analysed at 14 days post II. Antibody response to HAV was monitored 14 days post III.

NMRI mice

Groups of 10 mice were immunised intraperitoneally once with HAV/HBs formulations (½ HD). Antibody response to Hbs and HAV were monitored by ELISA at 28 days post injection.

Formulations

| Group | Vaccine lot | Formulation |
|---|---|---|
| 1 | HAB112B6 | HBs 20 μg/AlPO4 + HAV 720/Al(OH)3 |
| 2 | DHAB713 | HBs 20 μg/AlPO4/MPL 50 + HAV 1440/Al(OH)3 |
| 3 | DHAB717 | HBs 20 μg/AlPO4 + MPL 50/Al(OH)3 + HAV 720/Al(OH)3 |
| 4 | DHAB718 | HBs 20 μg/AlPO4 + MPL 50/AlPO4 + HAV 720/Al(OH)3 |
| 5 | DHAB716 | HBs 20 μg/AlPO4/MPL 50 + HAV 720/Al(OH)3 |

HAV Mouse Serology

Quantitation of anti-Hepatitis A Virus antigen (HAV) antibody was performed using Enzygnost kit from Behring (ref: OQECI11). This assay is an ELISA based on the competitive test principle, run in one step and initially developed for human serology.

Two-fold dilution of mice sera (4 dilutions starting at 1/10) human anti-HAV reference (8 dilutions starting at 80 mIU/ml) and controls were performed in anti-HAV negative human sera. Mixtures of test/control samples (25 μl), HAV antigen solution (50 μl) and anti-HAV mouse monoclonal conjugated with peroxidase (50 μl of 1/41 dilution performed in conjugate buffer) were incubated on HAV pre-coated microplates for 2 hrs at 37° C. The plates were then washed and incubated for 30 min with a solution of TMB (100 μl). The reaction was stopped with $H_2SO_4$ 0.5N and read at $^{450}/_{620}$ nm.

Anti-HAV antibody titers were calculated from the reference by SoftmaxPro (using a four parameters equation) and expressed in mIU/ml.

Results

The results are shown in FIG. 1.

In FIG. 1*a* results demonstrate that formulations containing MPL induce significantly higher antibody responses to the hepatitis A component than the aluminum salt group alone. Similarly the results shown in FIG. 1*b* demonstrate that MPL containing formulations induce higher antibody titres to HbsAg.

Example 5

Clinical Studies

HAV/HBs (HAB) formulations were administered to healthy subjects.

Serum titres of anti-HAV antibodies were measured by ELISA (Enzymun test from Boehringer Mannheim) and anti-HBs antibodies by radioimmunoassay (RIA) using test kit AUSAB-Abbott. The assay cut-off for anti-HAV antibodies was 33 mIU/ml and the assay cut-off for anti-HBs antibodies was 1 mIUml.

Subjects with anti -HAV antibody titres of 33 mIU/ml were considered to be seropositive for anti-HAV antibodies. Subjects with anti-HBs antibody titres 1 mIU/ml were considered to be seropositive for anti-HBs antibodies. Seroprotection rate for anti-HBs was defined as the ratio of subjects with anti-HBs titres 10 mIU/ml.

Vaccine lots

|  | Commercial TwinrixTM (adult) Group 1 | Combined HAB/MPL candidate Group 3 |
|---|---|---|
| Lot n° | HAB 116C4/M1 | DHAB 713A2 |
| Inactivated hepA (strain HM175-RIT 4380) | at least 720 EL.U | at least 1440 (new process) EL.U |
| Recombinant HBsAg | 20 μg | 20 μg |
| MPL | — | 50 μg |
| Al salt | 0.45 mg | 0.5 mg |
| Volume/dose | 1.0 ml | 0.5 ml |

Results:

In this phase I clinical trial where HAB/MPL was administered to healthy subjects, there is a marked effect of MPL acting as immunostimulant on the immune response.

MPL has a clear effect on anti-HAV kinetics. It induces a faster and stronger immune response with a marked anamnestic response observed at Mth 6.5 and Mth 7 (i.e. 14 and 30 days respectively, after the last vaccine dose).

Within the limitations of the study, it can be concluded that the candidate HAB/MPL vaccine exhibited a very good safety and reactogenicity profile. It was very immunogenic after a full vaccination course of 2 doses in the study cohort of healthy adults aged 18–40 years. There was a strong prirning and faster immune response to both hep A & B antigens.

1. Anti-HAV Kinetics

|  |  | D7 | D9 | D11 | D13 | D15 |
|---|---|---|---|---|---|---|
| Twinrix 720/20 | SC % | 5 | 10 | 30 | 65 | 74 |
| 0, 1, 6 M | GMT | 35 | 41 | 71 | 84 | 176 |
| N = 20 |  |  |  |  |  |  |
| 1440 HAV(new | SC % | 10 | 60 | 95 | 100 | 100 |
| process) | GMT | 37 | 43 | 125 | 316 | 569 |
| 20 μg HBsAg |  |  |  |  |  |  |
| 50 μg MPL (mixed) |  |  |  |  |  |  |
| 0.5 mg Alum – 0, 6 M |  |  |  |  |  |  |
| N = 20 |  |  |  |  |  |  |

2. Anti-HAV Titers

|  |  | D15 | M1 | M7 |
|---|---|---|---|---|
| Twinrix 720/20 | GMT | 176 | 349 | 7107 |
| 0, 1, 6 M |  |  |  |  |
| N = 50 |  |  |  |  |
| 1440 HAV(new | GMT | 569 | 888 | 13386 |
| process) |  |  |  |  |
| 20 μg HBsAg |  |  |  |  |
| 50 μg MPL (mixed) |  |  |  |  |
| 0.5 mg Alum – 0, 6 M |  |  |  |  |
| N = 50 |  |  |  |  |

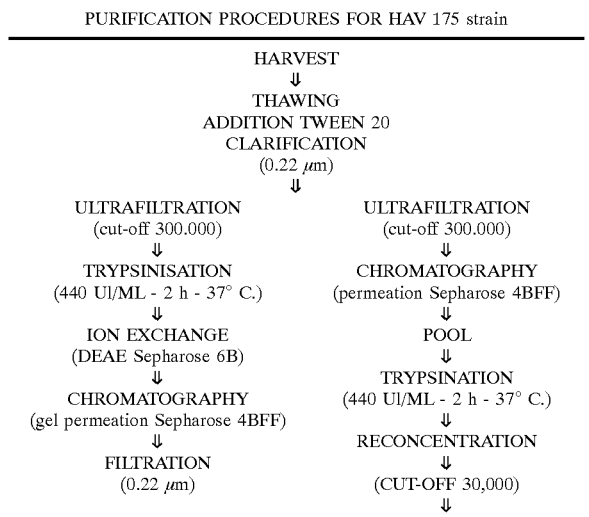

SCHEME 1

PURIFICATION PROCEDURES FOR HAV 175 strain

HARVEST
⇓
THAWING
ADDITION TWEEN 20
CLARIFICATION
(0.22 μm)
⇓

| ULTRAFILTRATION | ULTRAFILTRATION |
|---|---|
| (cut-off 300.000) | (cut-off 300.000) |
| ⇓ | ⇓ |
| TRYPSINISATION | CHROMATOGRAPHY |
| (440 Ul/ML - 2 h - 37° C.) | (permeation Sepharose 4BFF) |
| ⇓ | ⇓ |
| ION EXCHANGE | POOL |
| (DEAE Sepharose 6B) | ⇓ |
| ⇓ | TRYPSINATION |
| CHROMATOGRAPHY | (440 Ul/ML - 2 h - 37° C.) |
| (gel permeation Sepharose 4BFF) | ⇓ |
| ⇓ | RECONCENTRATION |
| FILTRATION | ⇓ |
| (0.22 μm) | (CUT-OFF 30,000) |
| ⇓ | ⇓ |

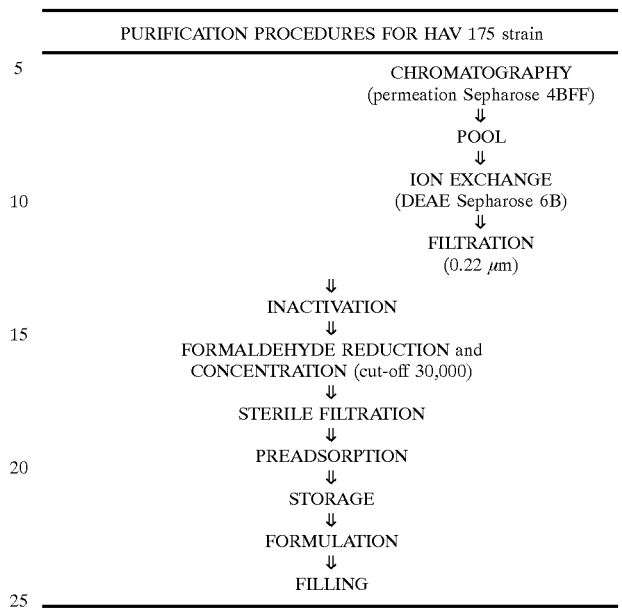

SCHEME 1-continued

PURIFICATION PROCEDURES FOR HAV 175 strain

CHROMATOGRAPHY
(permeation Sepharose 4BFF)
⇓
POOL
⇓
ION EXCHANGE
(DEAE Sepharose 6B)
⇓
FILTRATION
(0.22 μm)
⇓
INACTIVATION
⇓
FORMALDEHYDE REDUCTION and
CONCENTRATION (cut-off 30,000)
⇓
STERILE FILTRATION
⇓
PREADSORPTION
⇓
STORAGE
⇓
FORMULATION
⇓
FILLING

What is claimed is:

1. A process for the production of inactivated Hepatitis A virus substantially free of host cell contamination, the process comprising:

a) a culturing Hepatitis A virus and harvesting a hepatitis A preparation;

b) treating said hepatitis A preparation with a protease, thereafter;

c) separating intact virus from protease-digested protein; and d) inactivating said virus.

2. A process as claimed in claim 1, wherein the Hepatitis A virus is derived from HM-175 strain.

3. A process as claimed in claim 1, wherein the protease is trypsin.

4. A process as claimed in claims 1, wherein part c) includes a permeation chromatography step.

5. A process as claimed in claims 1, further comprising an ion exchange step after protease digestion.

* * * * *